United States Patent
Newberg

(10) Patent No.: US 6,345,640 B1
(45) Date of Patent: Feb. 12, 2002

(54) DIP TUBE VALVE ASSEMBLY

(75) Inventor: Douglas A. Newberg, Gambrills, MD (US)

(73) Assignee: NL Technologies, Ltd., Gambrills, MD (US)

( * ) Notice: Subject to any disclaimer, the term of this patent is extended or adjusted under 35 U.S.C. 154(b) by 0 days.

(21) Appl. No.: 09/471,252

(22) Filed: Dec. 23, 1999

Related U.S. Application Data

(60) Provisional application No. 60/113,936, filed on Dec. 24, 1998.

(51) Int. Cl.⁷ ................................................. F16K 1/44
(52) U.S. Cl. .................... 137/15.05; 137/240; 137/375; 251/144; 73/863.86
(58) Field of Search ................................ 137/240, 375, 137/15.05; 251/144, 319, 353; 73/863.86

(56) References Cited

U.S. PATENT DOCUMENTS

| | | | | |
|---|---|---|---|---|
| 711,609 | A | * 10/1902 | Woodnall | 251/353 |
| 1,351,780 | A | * 9/1920 | Mead | 251/353 |
| 1,397,220 | A | * 11/1921 | Lord | 251/353 |
| 2,841,314 | A | * 7/1958 | Munson et al. | 251/353 |
| 3,523,549 | A | * 8/1970 | Anderson | 251/353 |
| 3,693,647 | A | * 9/1972 | Saar | 137/363 |
| 3,871,400 | A | * 3/1975 | Thastrup | 137/363 |
| 4,346,611 | A | 8/1982 | Welker | |
| 4,458,543 | A | * 7/1984 | Mieth | 73/863.86 |
| 4,643,218 | A | * 2/1987 | Reed, Jr. | 137/237 |
| 4,702,275 | A | * 10/1987 | Ballun et al. | 137/556 |
| 4,708,160 | A | * 11/1987 | Sharp et al. | 137/368 |
| 4,804,164 | A | 2/1989 | Nakazawa et al. | |
| 4,822,570 | A | 4/1989 | Lerman et al. | |
| 4,909,271 | A | 3/1990 | Canaan et al. | |
| 4,911,412 | A | 3/1990 | Danko | |
| 5,096,029 | A | 3/1992 | Bauer et al. | |
| 5,152,500 | A | 10/1992 | Hoobyar et al. | |
| 5,296,197 | A | 3/1994 | Newberg et al. | |
| 5,370,146 | A | * 12/1994 | King et al. | 7/369 |
| 5,372,782 | A | 12/1994 | Karkantis et al. | |
| 5,525,301 | A | 6/1996 | Newberg et al. | |
| 5,794,644 | A | * 8/1998 | Paylor | 34/21 |
| 5,823,222 | A | * 10/1998 | Minshull et al. | 2/148 |
| 6,182,685 | B1 | * 2/2001 | Goff et al. | 137/340 |

* cited by examiner

Primary Examiner—A. Michael Chambers

(57) ABSTRACT

An apparatus for inoculating a sample to or withdrawing a sample from a vessel or conduit includes a body with an internal collection chamber formed therein. A valve operating rod is movable to open and close an orifice in the collection chamber. The mechanism used to reciprocate the valve operating rod to open and close the orifice can be either manual and automatic. Furthermore, a drain passage having an opening in communication with the collection chamber is located adjacent to or below the opening of the orifice. An inlet passage having an opening in communication with the collection chamber is located above the opening of the drain passage. A seal is formed between the movable valve operating rod and the body, thereby separating and isolating certain mechanical parts of the valve from certain other process-contact parts of the valve. The seal is formed by one of seal glands, o-rings, flexible diaphragms or other device. Finally, a insulating jacket is provided to insulate the inside chambers of the valve from its surroundings. The insulating jacket can be thermal, electrical, magnetic and/or chemical. Specifically, the insulation can be insulating coatings, multiple wall constructions and the selection of materials of construction according to their properties.

20 Claims, 6 Drawing Sheets

DIP TUBE VALVE ASSEMBLY

This application claims benefit to U.S. provisional application Ser. No. 60/113,936, filed Dec. 24, 1998.

BACKGROUND OF THE INVENTION

1. Field of the Invention

The present invention relates to the field of sampling, feeding or inoculating of material from or to a vessel or conduit.

2. Description of Related Art

Quality products require precise control of many phases of a production process. It is also true that it is necessary to maintain the integrity of the process and to protect the surroundings from the process. While many advances have been made in the development of sensors for measuring the condition of a specific process on-line which will aid in maintaining this process integrity, many of the characteristics of processes still need to be measured off-line through the physical and/or chemical analysis of an actual sample of the process. The removal of the sample from the process has to be conducted in a way that will preserve the integrity of the process, the surrounding environment as well as the integrity and character of the sample itself.

In a related but different procedure, many processes require inoculation of seed organisms or catalysts into a process to initiate the conversion of a set of substrate materials into other process intermediates or a final product or set of products. Sometimes this seed material is a live organism, a component of a live organism or another form of catalyst. In any case, these materials frequently need to be added to a process in a way that maintains the integrity of the process, the materials being added and their source, the integrity of the surrounding environment, or, perhaps, all of these.

There are examples of devices in the prior art that provide a means to deliver or withdraw materials from a process while maintaining the integrity of the process, the sample or the feed material or the surrounding environment but these devices are restricted in their effectiveness, particularly in their abilities to maintain the integrity or character of either the sampled material or material being added to the process because these devices have designs that are optimized for use in certain physical orientations. When used in orientations other than those they are designed for, these devices frequently suffer from the presence of crevices, particularly between component joints exposed to the process, and from design features that inhibit free flow and drainage of flowable materials through the device, resulting in pooling within the device. Both the crevices and pooling phenomena result in material carryover from one sampling, feeding or inoculation episode to the next, causing the deterioration in quality of any subsequent material introduced through sampling, feeding or inoculating into these devices.

It is also the case that some of these devices are not designed to be reused or, if they are designed for reuse, must be removed from the process and cleaned and sometimes resterilized before being able to be used again with the process.

There is a need for an apparatus that can be fitted, either permanently or removably, into a process which will allow materials to be fed, inoculated to or sampled from a process through a device principally designed to provide access to the process from above but which may provide reasonably good access to a process when installed at angles from vertical to horizontal. It is also desirable that an embodiment of this device provide a means by which it can be washed and sterilized in place and a means by which the thermal and electrical conditions inside the device be generally insulated from those of the process into which it is inserted. It is further desirable that the device, when placed in installations from vertical to horizontal relative to the process, be able to accumulate flowable materials occurring in the device in an area where they may be expelled or washed out by the introduction of other flowable materials under pressure coming either from the process or a second source through another access into the device.

In the existing art, there are examples of devices that provide a means for adding materials to the process but do not provide a means for washing and resterilizing in place and for effectively draining sampled material or cleansing, rinsing or sterilizing solutions from within the device.

SUMMARY OF THE INVENTION

Accordingly, it is an object of the present invention to provide a device which allows for the feeding or inoculating of a material into a process, and which can be easily washed and resterilized in place.

It is another object of the present invention to provide a device which can be used in an orientation from the vertical to the horizontal and which can still effectively drain sampled material or cleansing, rinsing or sterilizing solutions from within the device.

It is a further object of the present invention to provide a device which enhances the free flow of material through the device in order to prevent the pooling of the material within the device. This prevents the contamination of the sampled material, material added to the process, or the process itself.

It is yet another object of the present invention to provide a device which can be reused over and over again, and which can be cleaned or sterilized without having to remove the device from the process.

The valve of the present invention is designed primarily to take samples from a vertical installation although it can be used effectively at angles of installation down to horizontal. The valve works by providing a collection basin or well at a lower portion of the collection chamber of the valve body of the dip tube valve assembly. A drain passage opening is provided adjacent to the opening of the orifice where the orifice opens into the collection chamber in the valve body. By arranging the opening to the drain passage even with or lower than the inside margin of the orifice opening, a flowable material inside the valve body, including the collection chamber, the inlet or drain passages, will drain down into the opening of the drain passage. When this valve is installed at a positive angle from the horizontal up to and including the vertical, sample material will not passively drain out of it.

Material may be sampled through the valve by supplying overpressure to force material inside the vessel or conduit through the orifice and up and out through the drain passage. However, once the orifice is closed, this material will flow back down into the collection chamber of the valve. In order to fully remove sampled material from within the valve a flowable material must be fed through the inlet passage into the collection chamber after the sampling orifice has been resealed. The introduction of this material will displace or flush the sampled material collected in the bottom of the collection chamber, forcing the sampled material up and out of valve through the drain passage.

The collection basin or well formed at the bottom of the collection chamber enhances the removal of the sampled material, since the material remaining in the collection chamber flows into the collection basin or well to adjacent the opening of the drain passage. Therefore, when the flowable material is provided through the inlet, the sampled material which has collected at the opening of the drain passage can be easily removed.

In a first embodiment of the present invention, the axis of the inlet can be oriented non-parallel to a plane passing through the major diameter of an embodiment with a round internal collection chamber. This off-center introduction of the flowable material will create a vortex flow through the collection chamber, scouring the surfaces of the chamber and forcing any flowable material therein down to the opening in the drain passage and then up and out through the drain passage.

In a second embodiment of the present invention, the opening of the drain passage can be oriented in a similar but opposing fashion so as to open into the vortexing flow. The effect of this is to sweep material down, into and then up and out of the drain passage.

While the valve of the present invention is similar in many aspects to sample valve embodiments previously disclosed, one of which is the dependence on gravity to direct the flow of material down through the collection chamber and then down into the drain passage opening, the valve of the present invention differs in that previous designs were only capable of supplying the sampled material out of the valve through the drain passage to a sample vial simply by means of gravity flow. The dip tube valve assembly of the present invention; however, includes an active scouring motion provided by a second flowable material supplied through the inlet passage to generally remove and deliver all of the sampled material up through and out of the drain passage to a sample vial.

It should be noted that the device of the present invention can be used for sampling a material without an inlet passage. This can be accomplished through the use of over-pressure of the source of sampled material alone or through the use of over-pressured sample material followed by a second flowable material through the sampling orifice. While in the second instance, all of the sampled material might be removed up through the drain passage to a sample vial, in the first instance, once the sampling orifice is resealed, sampled materials in the interstices of the valve remain in the valve until either the next sampling episode or until other active methods are used to remove them.

The above objects have been accomplished by the dip tube valve assembly of the present invention. An apparatus for sampling or feeding a flowable material through a wall of a vessel or conduit includes a body; a collection chamber formed in said body; a drain passage, said drain passage having an opening operatively connected to said collection chamber; an orifice formed in said body and in communication with said collection chamber, said orifice being located generally adjacent the opening of the drain passage; and a sealing device for sealing and unsealing said orifice.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

DESCRIPTION OF THE PREFERRED EMBODIMENTS

Figure 1:
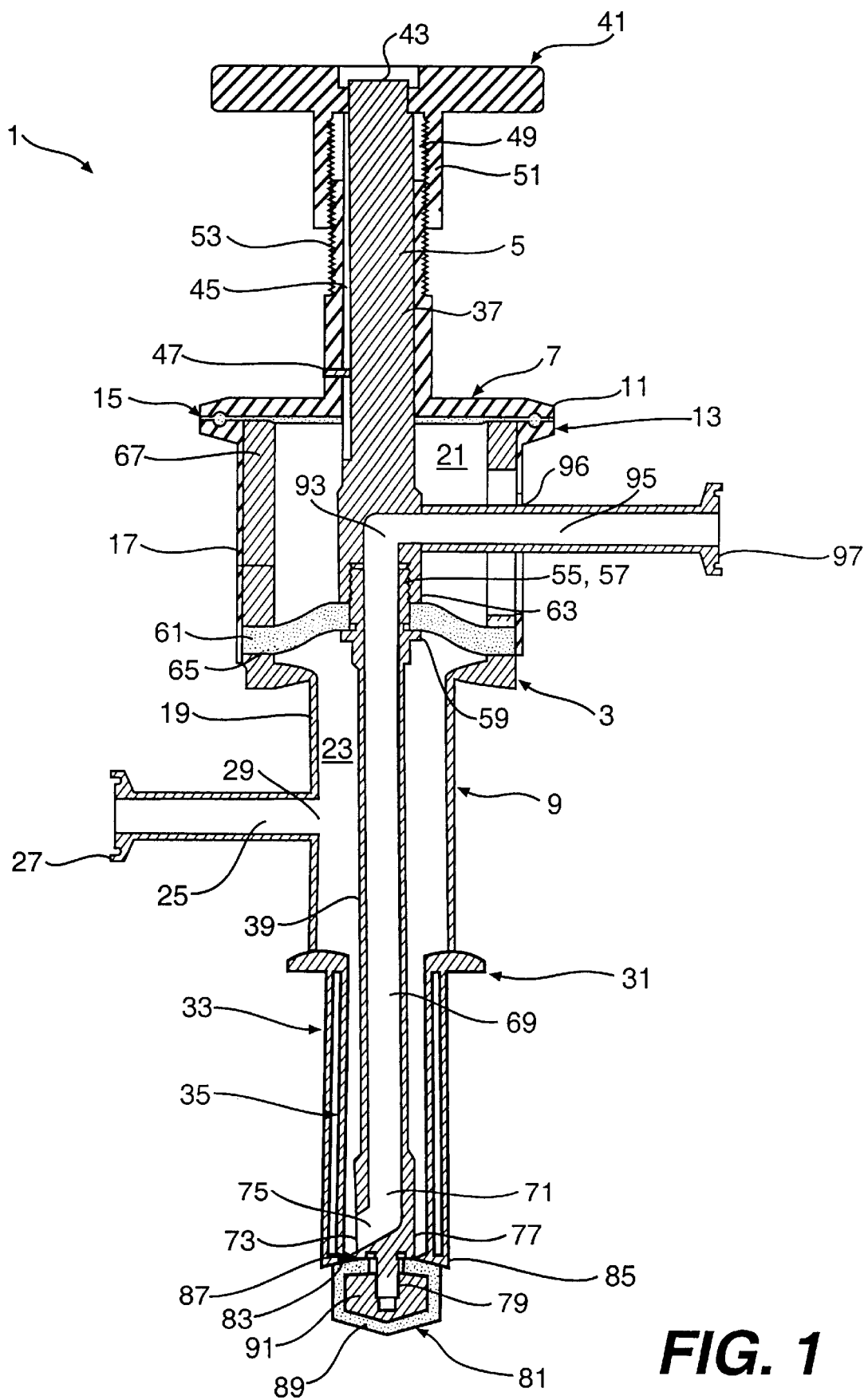
FIG. 1 is a cross-section of the first embodiment of the dip tube valve assembly of the present invention, wherein the valve is in the closed position.

The present invention will now be described with reference to the accompanying drawing. The same reference numerals have been used throughout the several views in order to identify the same or similar elements.

Figure 2:
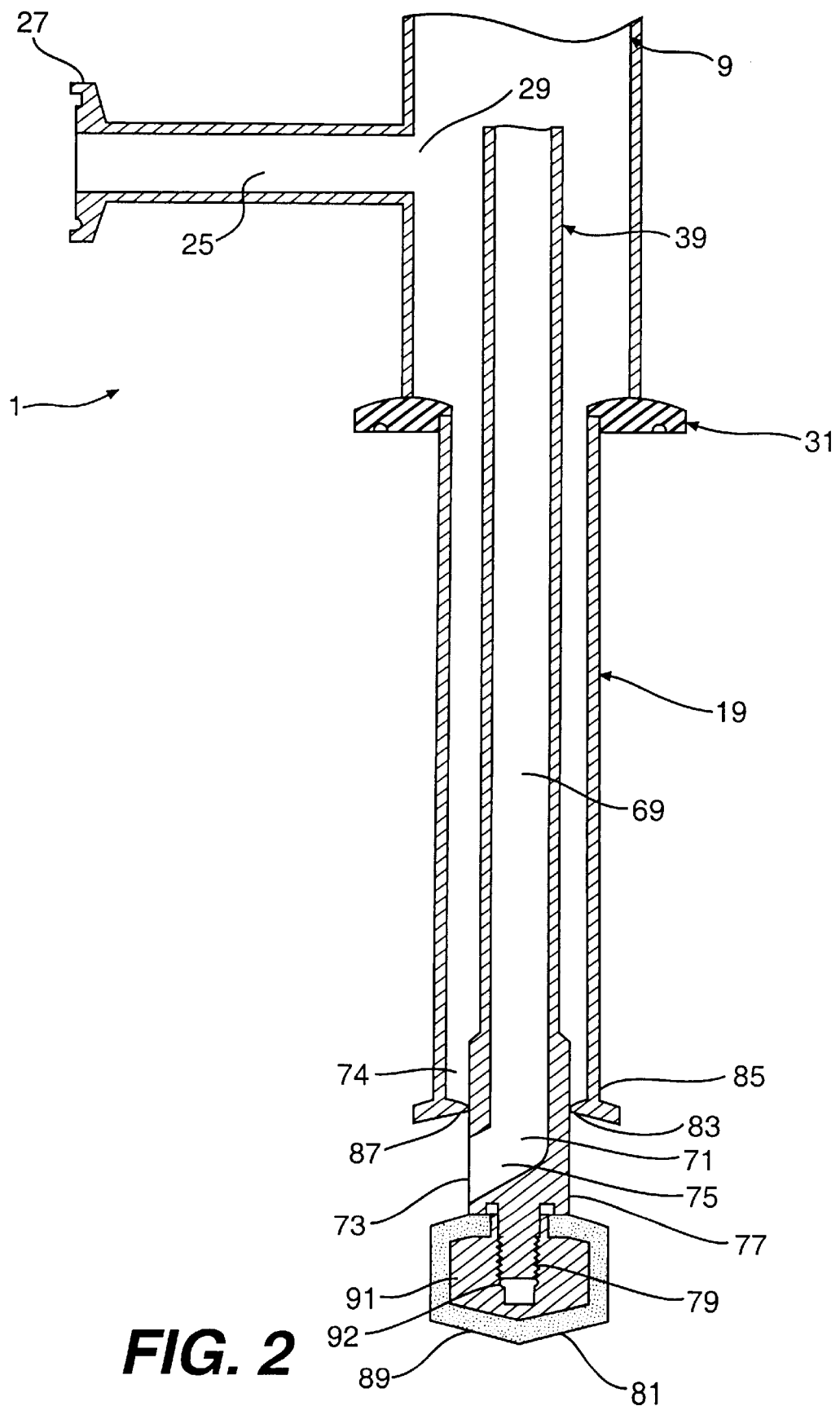
FIG. 2 is a detail of a lower portion of the embodiment of FIG. 1, wherein the valve is in the open position and no insulating jacket is included.

A first embodiment of the present invention will now be described with reference to FIGS. 1 and 2. FIG. 1 illustrates a cross-section of the first embodiment of the dip tube valve assembly of the present invention, wherein the valve is in the closed position. FIG. 2 is a detail of a lower portion of the embodiment of FIG. 1, wherein the valve is in the open position and no insulating jacket is included.

Referring to FIG. 1, the dip tube valve assembly 1 includes a body 3 and a valve operating rod or shaft 5 mounted for reciprocation within the body 3.

In the first embodiment, the body 3 includes a housing top 7 and a housing base 9 connected to each other through mutually engageable flanges 11 and 13 formed on the housing top 7 and housing base 9, respectively. The flanges are preferably secured together by a clamp (not illustrated); however, any other fastening means can be used, such as a plurality of bolts extending through holes formed in the perimeter of the flanges 11 and 13. A gasket 15 may be located between the flanges 11 and 13 in order to provide a sealed connection between the housing top 7 and the housing base 9.

The housing base 9 includes a large diameter portion 17 and a small diameter portion 19 having cavities 21 and 23, respectively formed therein. The small diameter portion 19 includes an inlet passage 25 connected thereto for introduction of the flowable material into the cavity 23. The inlet passage 25 includes a flange 27 formed thereon for connecting to a source of the flowable material. Furthermore, the inlet passage 25 includes an opening 29 into the cavity 23. The inlet passage 25 is preferably located offset with respect to a plane passing through an axis of the small diameter portion 19 in order to create a vortex flow through the collection chamber. The vortex flow through the collection chamber scours the surfaces of the collection chamber and forces any flowable material therein down to the opening in the drain passage and then up and out through the drain passage.

A flange 31 is mounted at an intermediate position on the small diameter portion 19 for connecting the dip tube valve assembly 1 to the wall of a vessel or conduit (not illustrated in FIGS. 1 and 2). As is well known, the vessel or conduit would include a flange (not illustrated) for cooperating with the flange 31 formed on the small diameter portion 19 for removably securing the dip tube valve assembly to the vessel or conduit. Alternatively, the body 3 may be welded or otherwise permanently affixed into the wall of the vessel or conduit somewhere along the outside surface of the small diameter portion 19 below the inlet passage 25. There would be a smooth transition along the outside surface of the small diameter portion 19 in this case, since it would be unnecessary to provide the flange 31.

It is noted that the "large diameter" and "small diameter" character of the portions 17 and 19 are not important. The only requirement is that the portions 17 and 19 include cavities 21 and 23 of a sufficient size to fit the mechanical elements within cavity 21 and to provide sufficient space for the free flow of material within cavity 23. It is possible to make the small diameter portion 19 larger than the large diameter portion 17, depending upon the application.

Referring specifically to FIG. 1, the small diameter portion 19 may also include an insulating jacket 33 which is formed by securing a cylinder around the small diameter portion, the cylinder having an inside diameter which is larger than an outside diameter of the small diameter portion 19. A space 35 is formed between the insulating jacket 33 and the small diameter portion which can be filled with an insulating material or can merely be an air space. The insulating jacket 33 is not a required element of the present invention. Referring to FIG. 2, the dip tube valve assembly is illustrated without an insulating jacket 33. The insulating jacket is useful in applications which require thermal, electrical or other insulation to insulate the internal portion of the dip tube valve assembly from the surrounding environment. In view of this, the insulating jacket can also be thermal, electrical, magnetic and/or chemical. Furthermore, the insulation can be carried out through the use of insulating coatings or other materials of construction selected according to their properties, as well as the multiple wall construction of the present embodiment.

Referring again to FIG. 1, the shaft 5 according to the first embodiment of the present invention includes a main shaft portion 37 and a drain passage portion 39. The main shaft portion 37 includes a handwheel 41 mounted on an end 43 thereof. A groove 45 is formed along one side of the main shaft portion 37 which engages with a pin 47 secured to the housing top 7. The pin 47 prevents rotation of the main shaft portion 37, but allows the main shaft 37 to reciprocate with respect to the housing top 7.

The handwheel 41 includes an aperture 49 formed therein which includes threads 51 for threadably engaging threads 53 formed on an outside surface of the housing top 7. The handwheel 41 is mounted to the end 43 of the main shaft portion 37 such that no rotation occurs between the handwheel 41 and the main shaft portion 37. The attachment of the handwheel 41 to the main shaft portion 37 can be accomplished by any means which prevents rotation between the two members including press fitting, a screw, etc., all of which would be readily apparent to the ordinary artisan.

It is also noted that the present invention is not limited to the use of a handwheel; but any mechanism for causing reciprocating motion of the shaft 5 can be used. Furthermore, it is within the scope of the present invention to provide an automatic device rather than the manual handwheel illustrated.

The drain passage portion 39 of the shaft 5 is connected to the main shaft portion 37 by cooperating threads 55 and 57 respectively formed on the main shaft portion 37 and the drain passage portion 39. The drain passage portion 39 includes a shoulder 59 formed thereon for securing a diaphragm 61 between the shoulder 59 and an end 63 of the main shaft portion 37. The diaphragm 61 is secured around an outside perimeter thereof by being sandwiched between a shoulder portion 65 formed on the large diameter portion 17 and an inner cylinder 67 fitted within the cavity 21 of the large diameter portion 17. The inner cylinder 67 is held in contact with the diaphragm 61 by the flange 11 when the flanges 11 and 13 are connected to each other. The inner cylinder 67 can be removed from the large diameter portion when the flanges 11 and 13 are separated from each other. This provides for easy removal and replacement of the diaphragm 61 in the case of wear. The diaphragm seals the cavity 21 formed in the large diameter portion 17 of the housing base 9 from the small diameter portion 19, while allowing the shaft 5 to reciprocate within the housing base 9.

It is noted that an o-ring (not illustrated) can be used as an alternative to the diaphragm of FIG. 1. Furthermore, any other arrangement that provides an adequate seal between the shaft 5 and the housing base 9 can be used as well.

Referring to FIG. 2, the drain passage portion 39 also includes a drain passage 69 formed therethrough. A lower end 71 of the drain passage 69 includes a radial portion 75 which extends from a center of the drain passage portion 39 to an opening 73 formed on the outside surface of the drain passage portion 39. The opening 73 is in communication with a collection chamber 74 formed at a bottom of the cavity 23 in the small diameter portion 19 of the housing base 9 when the dip tube valve assembly is in the closed position as illustrated in FIG. 1. However, the opening 73 is in communication with an inside of the vessel or conduit (not illustrated in FIGS. 1 and 2) when the dip tube valve assembly 1 is in the open position as illustrated in FIG. 2.

The opening of the drain passage can be oriented offset with respect to a plane passing through the central axis of the drain passage in a similar but opposing fashion to the inlet passage so as to open into the vortexing flow. The effect of this is to sweep material down, into and then up and out of the drain passage.

It should be noted that a collection basin or well is formed at the bottom of the collection chamber 74 at the lowest point of the collection chamber 74. In applications particularly useful for sampling, it is preferable to provide the lowest point in the collection chamber 74 immediately adjacent to the opening 73 of the drain passage 69. This will ensure that the sampled material will accumulate at the opening 73 in order to enhance the removal of the material which has collected therein.

Furthermore, as best illustrated in FIG. 2, a screw portion 79 is formed on a lower end 77 of the drain passage portion 39. This screw portion 79 is for threadably receiving a sealing tip 81 thereon. The sealing tip 81 is for sealing an orifice 83 formed at a lower end 85 of the small diameter portion 19 of the housing base 9 and includes a flexible outer covering 89 and a rigid internal portion 91. The rigid internal portion 91 includes threads 92 formed therein for cooperating with the screw portion 79. In addition, the lower end 85 of the small diameter portion 19 includes an internal shoulder 87 formed thereon for engaging with the flexible outer covering 89 of the sealing tip 81 in order to provide a sufficient seal therebetween.

It is noted that the sealing tip need not be secured in the manner illustrated in FIG. 1, but may be secured in any other manner that provides a sufficient connection between the drain passage portion 39 and the sealing tip 81. For example, a nut may be threadably attached to the screw portion 79 from a lower surface of the sealing tip 81. Furthermore, the seal between the orifice and the bottom of the shaft 5 need not be performed with the sealing tip 81 illustrated in FIGS. 1 and 2. It is only necessary that the shaft 5 include a sealing tip that can be brought into cooperation with the orifice in order to form a seal therebetween. This can be accomplished by a soft flexible seal as in FIGS. 1 and 2, a metal-to-metal seal, or other sealing device.

Referring again to FIG. 1, the main shaft portion 37 includes a drain passage 93 formed therethrough. The drain passage 93 communicates the drain passage 69 in the drain passage portion 39 to a drain outlet 95. The drain outlet 95 can be welded to the main shaft portion 37 or can include threads (not illustrated) for engaging with threads (not illustrated) formed in the main shaft portion 37. The drain outlet 95 includes a flange 97 formed thereon for connecting the drain outlet 95 to other equipment downstream for processing the flowable material supplied therethrough. The drain outlet 95 extends through an aperture 96 formed in the large diameter portion 17. The aperture 96 is elongated in the longitudinal direction of the body 3 in order to provide for reciprocating movement of the drain outlet 95 along with the reciprocating movement of the shaft 5. It is noted that the aperture 96 need only be large enough to allow for movement of the drain outlet 95.

Alternatively, the drain outlet 95 can be attached directly to the large diameter portion 17. A flexible tube can then attach the inside of the drain outlet 95 to the drain passage 93 formed in the main shaft portion 37. The tube can be coiled in the cavity 21 in order to provide sufficient space to reciprocate the shaft 5.

The operation of the first embodiment of the present invention will now be described. Referring to FIG. 1, the dip tube valve assembly 1 is in the closed position and ready for a feeding or a sampling process to take place. The sealing tip 81 is positioned in contact with the internal shoulder 87 of the small diameter portion 19, forming a seal therebetween.

The valve is opened by rotating the handwheel 41 to move the shaft 5 in a longitudinal direction to position the sealing tip in the position illustrated in FIG. 2. If a feeding process is desired, the flowable material is fed through the inlet passage 25, through the collection chamber 74, through the orifice 83 and into the vessel or conduit (not illustrated in FIGS. 1 and 2). If a sampling process is desired, the inlet passage 25 is closed upstream from the valve. This causes a vapor lock which inhibits back-filling into the cavity 23 of the small diameter portion 19 and causes the sampled material to flow up and out of the drain passage 69, rather than the inlet passage 25. Once the material is completely fed into the vessel or conduit or the sample is removed from the vessel or conduit, the valve is closed by rotating the handwheel 41 in an opposite direction to move the shaft 5 to the position illustrated in FIG. 1. Any excess feeding or sampled material will drain down into the collection chamber, and due to the location of the opening 73 of the drain passage 69, the material will collect at the bottom of the collection chamber adjacent to the opening 73 of the drain passage 69.

Some processes or some steps of processes are carried out at lower pressures than ambient. As a result, a vacuum may be necessary to draw the sample up and out of the vessel or conduit and through the drain passage 69.

If a sampling process was performed, it may be desirable to remove any of the remaining sample material which has collected adjacent the opening 73. This is accomplished by feeding a flowable material, such as a gas, through the inlet passage 25. Since the axis of the inlet passage 25 is oriented non-parallel to a plane passing through the major diameter of the body 3 of the dip tube valve assembly 1, the flowable material creates a vortex flow through the cavity 23 to the opening 73 and through the drain passage 69. The vortex flow scours the surfaces of the inlet passage 25, cavity 23 and drain passage 69 in order to remove the remaining sample therefrom.

If it is desired to clean or sterilize the dip tube valve assembly, a cleaning or sterilizing solution can be fed through the inlet passage 25 and out of the drain passage 69. If this cleaning or sterilizing solution is a liquid and it is desired to remove remaining solution from the collection chamber, it is possible to force the remaining solution therefrom by providing a flowable material through the inlet 25 in the same manner as above.

Figure 3:
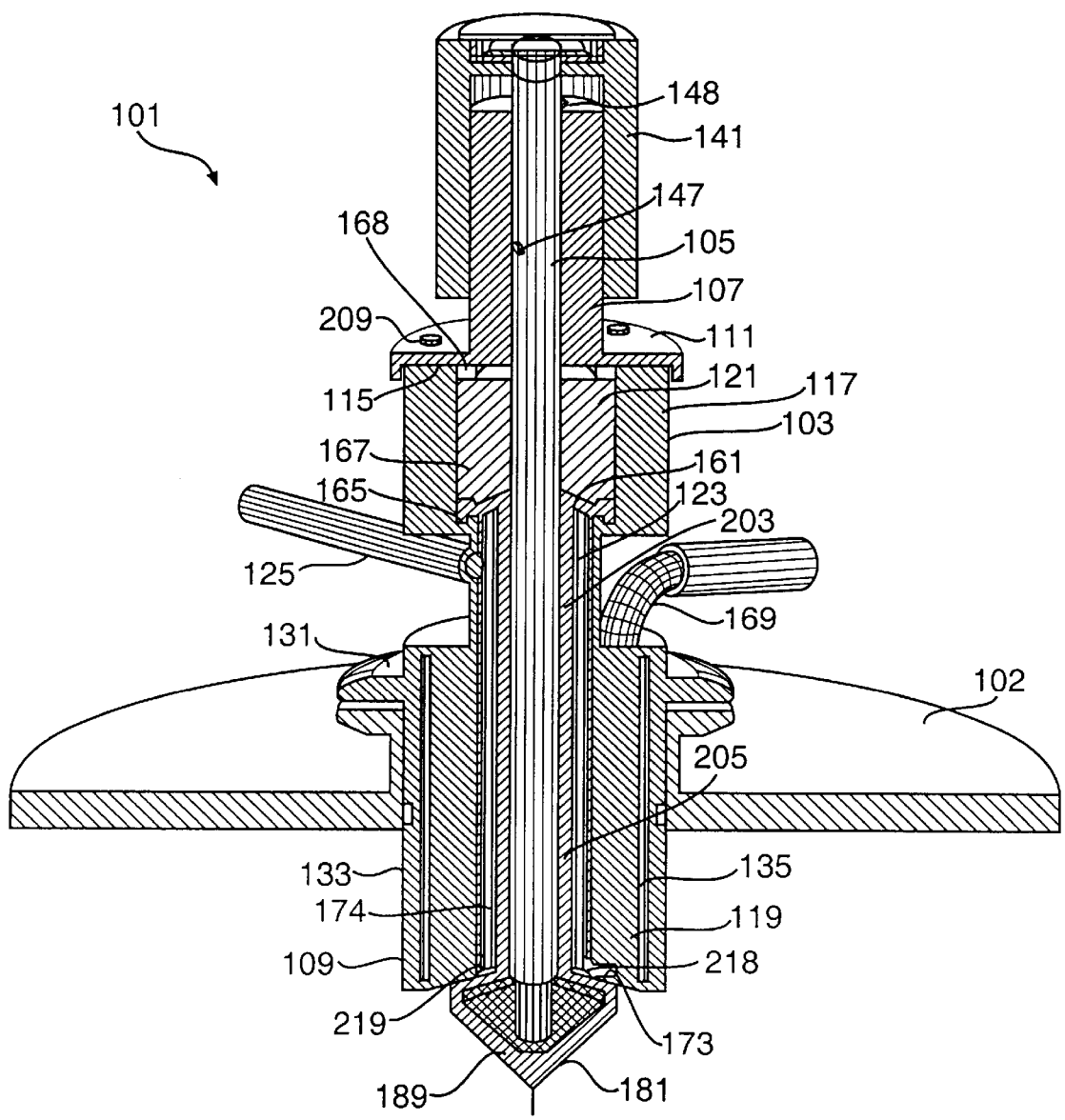
FIG. 3 is a cross-section of the dip tube valve assembly according to a second embodiment of the present invention, wherein the valve is illustrated in a closed position.
Figure 4:
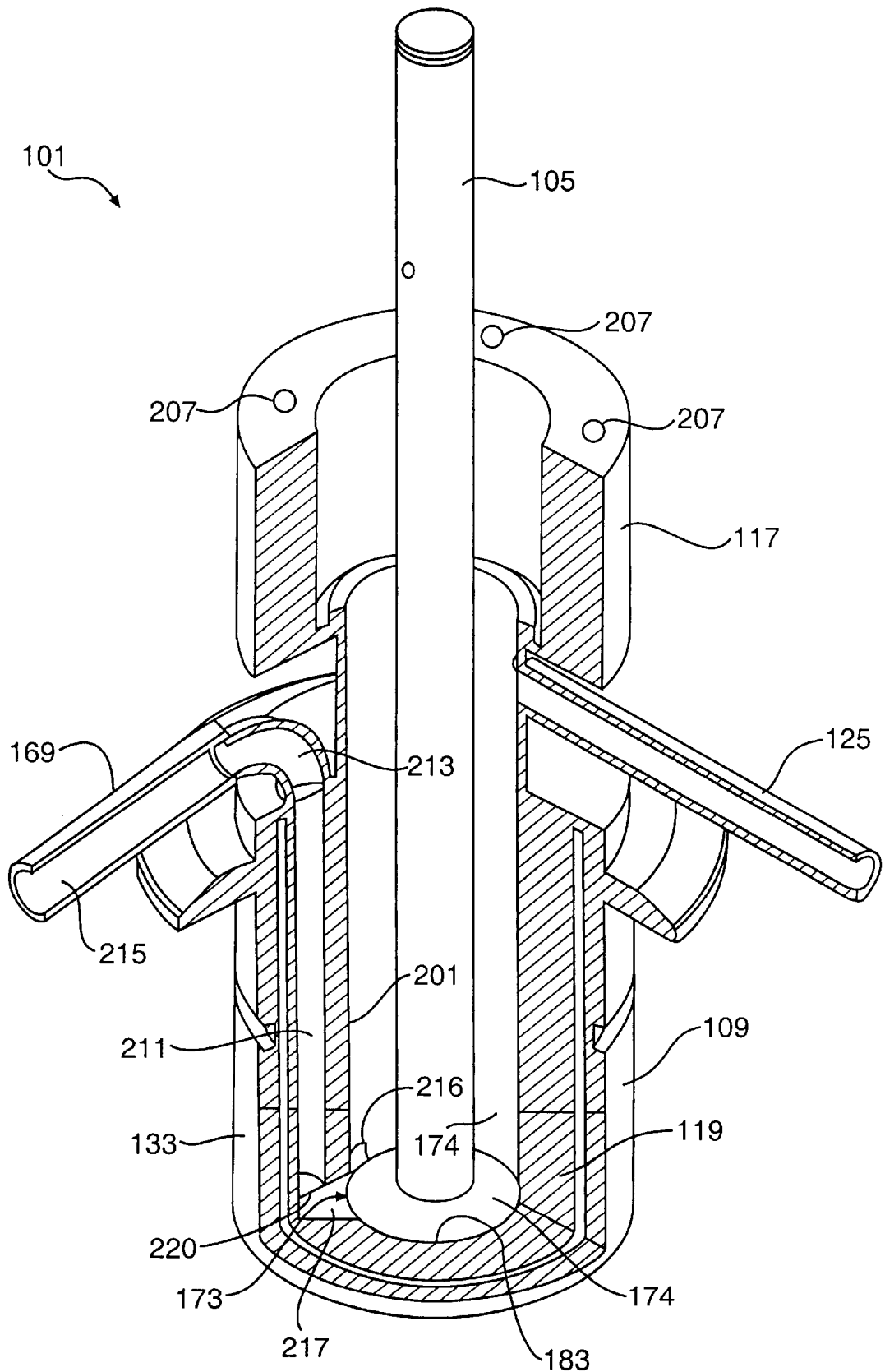
FIG. 4 is a cross-section of the second embodiment of the present invention through the drain passage and the inlet passage.
Figure 5:
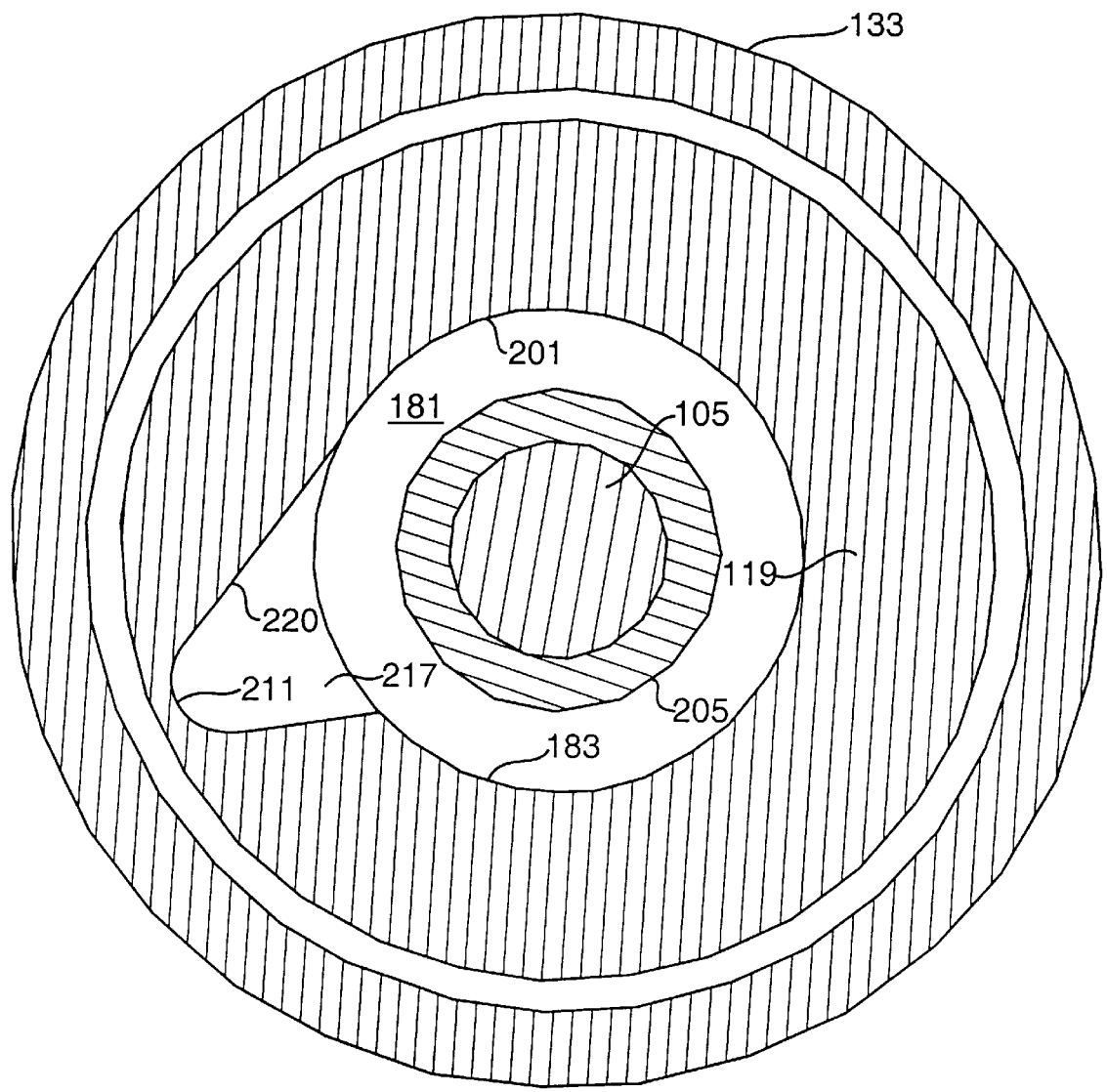
FIG. 5 is a cross-section through the lower horizontal section of the drain passage.

A second embodiment of the present invention will now be described with reference to FIGS. 3–5. FIG. 3 is a cross-section of the dip tube valve assembly according to the second embodiment wherein the valve is illustrated in the closed position. FIG. 4 is a cross-section of the second embodiment through the drain passage and the inlet passage. FIG. 4 is illustrated with several of the elements removed, including the housing top, sealing tip and handwheel, for ease of understanding. FIG. 5 is a cross-section of FIG. 4 through the lower horizontal section of the drain passage.

The second embodiment of the present invention operates substantially the same as the first embodiment; however, the drain passage is located in the body of the dip tube valve assembly rather than in the reciprocating shaft. Elements which are the same as or similar to the first embodiment have been identified by the same reference numerals with 100 added thereto.

Referring to FIG. 3, the dip tube valve assembly 101 is secured to a vessel or conduit 102 through a flange 13 1 formed on the small diameter portion 119. As noted above, a conventional vessel or conduit typically includes a flange formed thereon for easy installation of the dip tube valve assembly 101 of the present invention.

Referring to FIGS. 3 and 4, the dip tube valve assembly 101 includes a drain passage 169 formed in the small diameter portion 119 of the housing base 109. The opening 173 of the drain passage 169 is formed on an inside wall 201 of the small diameter portion 119 adjacent to the orifice 183. Furthermore, the inlet passage 125 is formed in the small diameter portion 119 at a location above the location of the opening 173.

Referring to FIG. 3, the shaft 105 is a solid shaft which extends from the handwheel 141 to the sealing tip 181. It is unnecessary to provide multiple pieces to the shaft 105, since there is no passageway formed inside the shaft 105 as in the first embodiment. Forming the drain passage in the housing base, rather than in the shaft provides the advantage of manufacturing the shaft with a smaller diameter than the shaft of the first embodiment. However, as can be readily understood, it is necessary to make the thickness of the wall of the small diameter portion 119 in the second embodiment larger in order to accommodate the drain passage 169.

The second embodiment illustrated in FIG. 3 also includes a one-piece member 203 that acts as the diaphragm 61 and the flexible outer covering 89 of the first embodiment. Specifically, the one-piece member 203 includes a diaphragm portion 161 and a flexible outer covering 189. In addition, the one-piece member 203 includes a connecting portion 205 which connects the diaphragm portion 161 to the flexible outer covering 189. The one-piece member 203 of the second embodiment is advantageous, since only one piece is necessary to seal the orifice 183 and the end of the small diameter portion 119 adjacent to the large diameter portion 117. However, it will be readily apparent that the diaphragm 61 and the flexible outer covering 89 of the first embodiment can be substituted in the second embodiment and the one-piece member 203 of the second embodiment can be used in the first embodiment.

FIG. 3 also includes an alternative way to secure the housing top 107 to the housing base 109. A flange 111 is formed on the lower end of the housing top 107. Furthermore, a plurality of threaded holes 207 (see FIG. 4) are formed in the upper surface of the housing base 109. The flange 111 also includes holes (not illustrated) corresponding to the threaded holes 207 in the housing base 109. A plurality of screw 209 are fitted in the threaded holes 207 to fasten the flange 111 to the housing base 109. A gasket 115 may also be included between the flange 111 and the housing base 109 for proper sealing. Gasket 115 is not always necessary; however, it does help to form a second seal with the environment. It is noted that the above alternative can also be used in the first embodiment and the flanges and clamp of the first embodiment can be used in the second embodiment.

In FIG. 3, an alternative arrangement is illustrated to hold the diaphragm portion 161 in contact with the shoulder portion 165 of the large diameter portion 117. A cylindrical member 167 has an aperture formed therein for receiving the shaft 105 and a bottom surface having a conical shape corresponding to the upper surface of the diaphragm portion 161. Furthermore, a cylindrical member 168 is located above the cylindrical member 167 in order to force the diaphragm portion into contact with the shoulder portion 165 when the housing top 107 is connected to the housing base 109. It should be noted that the cylindrical member 168 is not required, since the flange 111 of the housing top 107 can directly contact the cylindrical member 167 to hold the diaphragm portion 161 in place.

As an alternative to preventing rotation of the shaft 105 with respect to the housing top 107, FIG. 3 illustrates a pin 147 fixed to the shaft 105 for engaging a keyway 148 formed in the housing top 107. Specifically, an aperture is formed extending through the shaft 105. This aperture receives pin 147 such that the pin extends outwardly from the shaft 105 on opposite sides of the shaft 105 (only one side of the pin 147 is illustrated). The ends of the pin engage in keyways 148 formed in the housing top 107 (only one keyway is illustrated). This allows the shaft 105 to reciprocate, while preventing the shaft from rotating when the handwheel 141 is rotated with respect to the housing top 107.

FIGS. 3 and 4 also illustrate the use of an insulating jacket 133 which forms a space between the small diameter portion 119 and an inside of the insulation jacket 133 in order to insulate the flowable material within the dip tube valve assembly or to insulate the process from the repeated hot steam resterilization of the dip tube valve assembly, usually performed after each sampling or feeding episode. As noted above, the insulation jacket 133 is only necessary if used in an environment that requires that the flowable material be insulated.

Referring to FIG. 4, the drain passage 169 is illustrated in cross-section. The drain passage 169 includes a vertical section 211, a curved portion 213, an upper horizontal section 215 and a lower horizontal section 217. It should be noted that the terms vertical and horizontal are used only for the purposes of description, since the dip tube valve assembly of the present invention is not required to be used in the position illustrated in the drawings. Furthermore, the upper horizontal section need not be horizontal, since it is preferable to have this section tilt downwardly in order to allow for material to drain out of the inside of the dip tube valve assembly 1 after the flowable material is turned off. The horizontal section 215 is attachable to downstream equipment in order to further process the flowable material. The lower horizontal section is formed by machining out the inside wall 201 of the small diameter portion 119. A generally square section of the inside wall 201 is cut out from the edge of the orifice 183 toward the vertical section 211 as illustrated in FIG. 3. The lower surface of the lower horizontal section 217 is generally even with or slightly angled downwardly from the edge of the orifice 183. Furthermore, an additional portion 216 of the inside wall 201 is cut out in order to form a smooth transition from the inner wall 201 to the drain passage 169 and to ensure that the opening 173 of the drain passage 169 is sufficiently wide. Accordingly, when the flowable material is fed through the inlet passage 125 to the opening 173 of the drain passage 169, the flowable material and any remaining feeding material, sampled material, or cleaning or sterilizing solution are thoroughly swept out of the drain passage 169.

In the second embodiment of the present invention, it is possible to prevent any pooling of the material therein other than immediately adjacent to the opening 173. Furthermore, since the lower horizontal section is formed generally even with the edge of the orifice 183, and actually may slope downwardly from the orifice 183, it is possible to provide for the pooling to occur in the lower horizontal section 217 itself, since the lower horizontal section 217 is lower than or even with the bottom of the collection chamber 174 in this embodiment. In the case where the lower horizontal section 217 is lower than the bottom of the collection chamber 174, the lower horizontal section 217 forms the collection well, since the lower horizontal section 217 is the lowest point within the collection chamber 174.

Referring to FIG. 3, since the sealing tip 181 is bulged upwardly at 219 due to the flexing of the flexible outer covering 189 when in the sealed position, any material remaining in the collection chamber 174 flows downwardly and into the horizontal section 217 of the drain passage 169.

The embodiment of FIGS. 3 and 4 is superior with regard to drainage of material being fed or sampled, even when the dip tube valve assembly is located such that the longitudinal direction of the body 103 is located nearly horizontal. Furthermore, this embodiment is superior with regard to cleaning of the interior between feeding and sampling episodes.

The above advantages of this embodiment can be particularly realized if the drain passage 169 is located very close to the collection chamber 174, i.e., the wall between the drain passage 169 and the collection chamber 174 is made very thin and the opening 173 is made as small as possible. However, it should be noted that the opening 173 should not be made smaller than the drain passage 169, since this would cause drain passage 169 to form a low energy "settling" zone with respect to the opening 173 and other possible areas.

Referring again to FIGS. 4 and 5, the drain passage 169 and the collection chamber 174 are connected by the opening 173 which includes the lower horizontal section 217. The lower horizontal section 217 includes a wall 218 having a lower margin 220 which is co-linear with a tangent to the inside surface 201 of the collection chamber 174 at the orifice 183. Furthermore, the lower margin 220 is co-linear with a tangent to the vertical section 211 of the drain passage 169. The tangents to the inside surface 201 and the vertical section 211 are coplanar with the bottom of the lower horizontal section 217. Furthermore, the lower margin 220 of the wall 218 is coplanar with a plane passing through the radial seal between the orifice 183 and the sealing tip 181. This configuration will make the dip tube valve assembly 101 the most effective at concentrating material for the purpose of cleaning and flushing near the opening 173 of the drain passage 169 at all angles of installation from the vertical down to near-horizontal, whether the device is used for sampling or feeding.

Referring specifically to FIG. 5, the lower margin 220 of the wall 218 is clearly illustrated extending from the inside wall 201 to the vertical section 211 of the drain passage 169. The bulging portion of the sealing tip 181 is raised with respect to the bottom of the lower horizontal section 217. Accordingly, the material in the collection chamber 174 flows from the sealing tip 181 and into the lower horizontal section 217.

The above aspects of the embodiment of FIGS. 3–5 can be better understood with the following explanation. If a flushing gas is introduced radially at the top of the collection chamber 174, the vortexing flow created will tend to scour the surfaces of the interior of the body 103 and carry the material down the inside wall 201, including the lower outside margin of the inside wall 201 where it is coplanar with the lower outside wall of the vertical section 211 of the drain passage 169 and the lower margin 220. Because of this, the material being carried along by the flushing gas will tend to flow into the drain passage and up and out of the body 103.

Since the drain passage in this embodiment is located radially outwardly from the collection chamber 174, the centripetal force caused by the vortexing flow naturally causes the material to be flushed to move outwardly toward the drain opening 173.

The drainage of the body 103 will only be most enhanced if it is installed at angles that tilt the body 103 back from the vertical on an axis formed by the lower margin 220 of the wall 218. Specifically, if the body 103 is installed at an angle less than the vertical, gravity will tend to collect the material along the lower margin 220 of the wall 218, i.e., at the intersection of the wall 218 and the bottom wall of the lower horizontal section 217.

Figure 6:
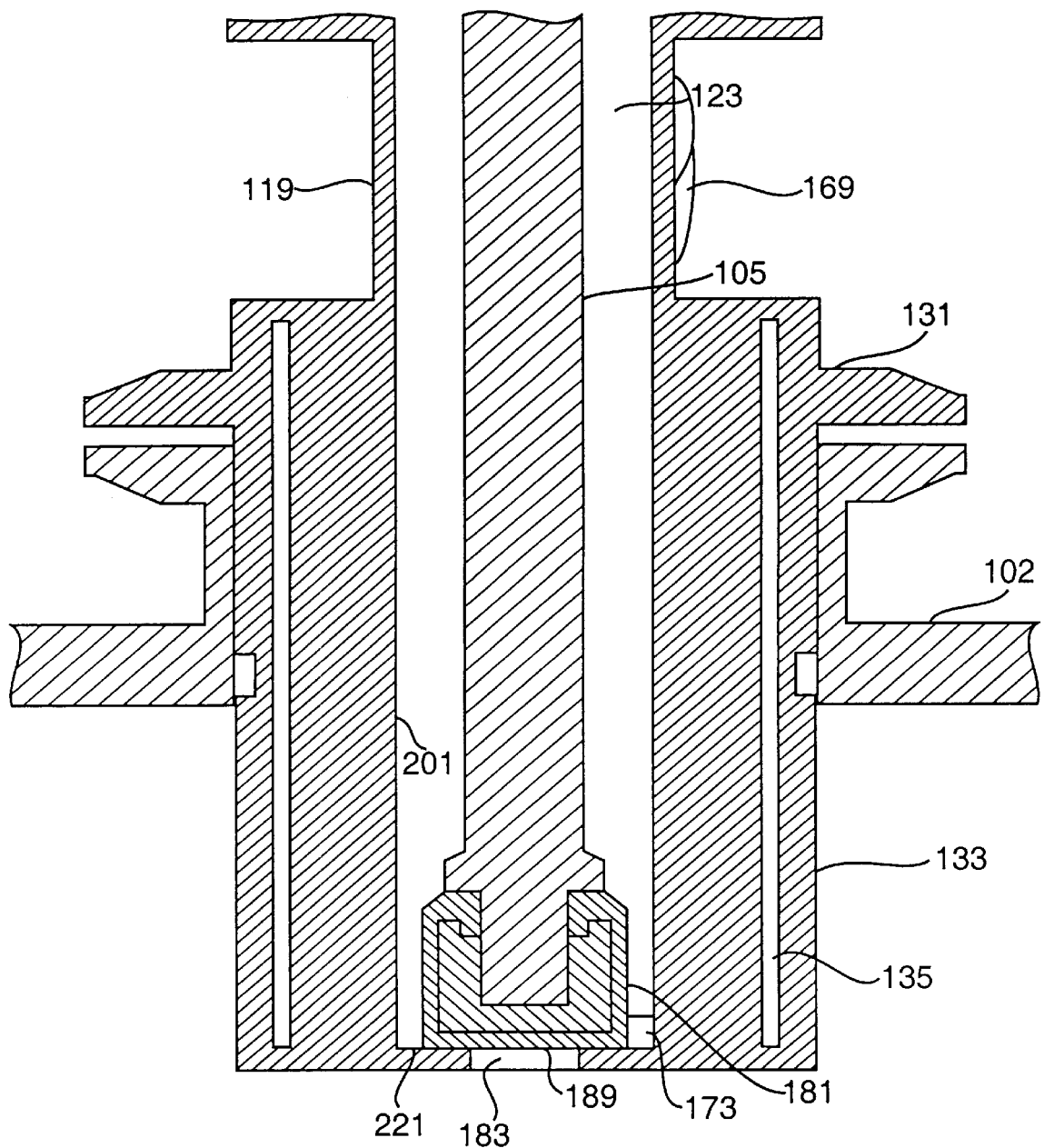
FIG. 6 is a cross-section of an alternative arrangement of the sealing tip of the present invention.

An alternative arrangement of the sealing tip of the present invention will now be described with reference to FIG. 6. The embodiment of FIG. 6 is generally the same as the embodiment of FIGS. 3 and 4, except for the fact that the shaft 105 is held in compression, rather than in tension to seal the orifice 183. Furthermore, the is sealing tip 181 is similar to the embodiment illustrated in FIGS. 1 and 2. The same reference numerals have been used in the embodiment of FIG. 6 that have been used in the embodiment of FIGS. 3 and 4.

Referring to FIG. 6, the sealing tip 181 is located in the closed position, wherein the flexible outer covering 189 is located in sealing contact with an inner shoulder 219 to seal the orifice 183. The inner shoulder 219 is formed by a wall extending inwardly from the inside wall 201 of the small diameter portion 119. In order to open the orifice 183, the shaft 105 is moved upwardly in FIG. 6 to move the sealing tip 181 away from the inner shoulder 219.

The inner shoulder is illustrated in FIG. 6 such that the upper surface 221 is generally horizontal. However, the upper surface 221 can be sloped either upwardly or downwardly, depending upon the application. If the upper surface 221 is sloped upwardly, the embodiment of FIG. 6 would be more advantageous if used as a sampling device, since the remaining sampled material would settle at the opening 173. If the upper surface 221 is sloped downwardly toward the orifice 183, the embodiment of FIG. 6 would be more advantageous if used a feeder/innoculator, since the material being fed would drain down into the orifice.

With regard to the insulating jacket 133 in FIG. 6, as noted above, the insulating jacket 133 is only necessary in applications that require insulation. Further to this, the space 135 formed by the insulating jacket is illustrated in the form of a cylinder. However, this space 135 can also include a horizontal opening extending inwardly from the space 135 toward the orifice 183 in order to further insulate the process from the dip tube valve assembly 101. A horizontal space would be most useful in pharmaceutical or food applications where the repeated sterilizing from steam can heat up the material in the vessel above a desired temperature.

It should be noted that the above embodiments in FIGS. 1–5 are illustrated as being formed from concentric cylindrical members secured to each other such that the shafts 5, 105 are located at the center of the cylinders. However, it is possible to form the body 3, 103 of the dip tube valve assembly 1, 101 of asymmetric or irregular shaped pieces. For example, in the embodiment of FIG. 4, it is possible to narrow the wall of the small diameter portion 119 on the side opposite to the drain passage 169 such that the shaft 105 is located more toward the side opposite to the drain passage 169. This will provide a dip tube valve assembly having a smaller cross-sectional area.

The invention being thus described, it will be obvious that the same may be varied in many ways. Such variations are not to be regarded as a departure from the spirit and scope of the invention and all such modifications as would be obvious to one skilled in the art are intended to be included within the scope of the following claims.

What is claimed is:

1. A method of removing material from an interior of a valve assembly, comprising:
   forming a body having a collection chamber formed therein;
   providing an inlet passage, a drain passage and an orifice in communication with said collection chamber, said drain passage and said orifice being generally adjacent to each other and said drain passage being located on a collection chamber side of said orifice;
   providing a sealing device for sealing and unsealing said orifice;
   forcing a flowable material through said inlet and said collection chamber and out of said drain passage to thereby remove the remaining material from the interior of the valve.

2. The method of cleaning an interior of a valve assembly according to claim 1, further comprising the step of locating said inlet passage at a position spaced from said drain passage and offset with respect to a plane passing through a central axis of said collection chamber, thereby forming a vortex in said collection chamber to scour the interior of the valve and carry the remaining material out of the drain passage.

3. The method of cleaning an interior of a valve assembly according to claim 2, further comprising the step of locating said opening of said drain passage offset with respect to a plane passing through a central axis of said drain passage in a direction opposite to the direction of offset of the inlet passage in order to position the opening into the vortexing flow.

4. The method of removing material from an interior of a valve assembly according to claim 1, further comprising the step of performing said step of forcing a flowable material when said sealing device is in a sealed position.

5. An apparatus for sampling or feeding a flowable material through a wall of a vessel or conduit comprising:
   a body;
   a collection chamber formed in said body;
   a drain passage, said drain passage having an opening operatively connected to said collection chamber;
   an orifice formed in said body and in communication with said collection chamber, said opening of said drain passage being located generally adjacent said orifice on a collection chamber side thereof; and
   a sealing device for sealing and unsealing said orifice.

6. The apparatus for sampling or feeding a flowable material through a wall of a vessel or conduit according to claim 5, further comprising an inlet passage formed in said body for receiving flowable material therethrough, said inlet passage having an opening in communication with said collection chamber.

7. The apparatus for sampling or feeding a flowable material through a wall of a vessel or conduit according to claim 6, wherein said inlet passage is located at a position above said drain passage, wherein the flowable material flows into said collection chamber through said inlet passage and out of said collection chamber through said drain passage.

8. The apparatus for sampling or feeding a flowable material through a wall of a vessel or conduit according to claim 6, wherein said inlet passage is positioned radially outwardly from said drain passage, wherein when said body is positioned in a horizontal direction, said opening of said inlet passage is positioned above said opening of said drain passage.

9. The apparatus for sampling or feeding a flowable material through a wall of a vessel or conduit according to claim 5, further comprising a shaft mounted for reciprocation within said body, said sealing device being mounted on an end of said shaft and said drain passage being formed within said shaft.

10. The apparatus for sampling or feeding a flowable material through a wall of a vessel or conduit according to claim 9, wherein said drain passage extends through a center of said shaft from said opening to an outlet of said drain passage, said outlet being formed in said shaft at a position spaced from said opening.

11. The apparatus for sampling or feeding a flowable material through a wall of a vessel or conduit according to claim 5, further comprising an insulating jacket formed on an outside surface of said body, said insulating jacket forming a space between said outside surface of said body and an inside surface of said insulating jacket.

12. The apparatus for sampling or feeding a flowable material through a wall of a vessel or conduit according to claim 5, wherein said opening of said drain passage includes a wall adjacent to said orifice and a wall remote therefrom, and said wall adjacent to said orifice is positioned generally even with a plane formed by an opening of said orifice.

13. The apparatus for sampling or feeding a flowable material through a wall of a vessel or conduit according to claim 5, wherein said opening of said drain passage includes a wall adjacent to said orifice and a wall remote therefrom, and said wall adjacent to said orifice is positioned generally offset from a plane formed by an opening of said orifice.

14. The apparatus for sampling or feeding a flowable material through a wall of a vessel or conduit according to claim 5, wherein said drain passage is formed in said body.

15. The apparatus for sampling or feeding a flowable material through a wall of a vessel or conduit according to claim 5, further comprising a collection well formed at a lowermost point of said collection chamber adjacent to said orifice and said opening of said drain passage, wherein the flowable material flows into said collection well to said opening of said drain passage.

16. The apparatus for sampling or feeding a flowable material through a wall of a vessel or conduit according to claim 5, said drain passage further comprising a horizontal section extending away from said opening of said drain passage and a portion extending away from said generally horizontal section.

17. The apparatus for sampling or feeding a flowable material through a wall of a vessel or conduit according to claim 16, wherein said generally horizontal section includes a wall having a lower margin extending from a wall of said collection chamber to a wall of said portion of said drain passage, said lower margin being co-linear with a tangent to said wall of said collection chamber and a tangent to said wall of said portion of said drain passage.

18. The apparatus for sampling or feeding a flowable material through a wall of a vessel or conduit according to claim 1, wherein said drain passage is in communication with said collection chamber when said sealing device is in a sealed position to allow the flowable material to flow from said collection chamber out said drain passage.

19. The apparatus for sampling or feeding a flowable material through a wall of a vessel or conduit according to claim 1, wherein said orifice forms a juncture between said collection chamber and the wall of the vessel or conduit, and sealing and unsealing said orifice allows flowable material to flow into or out of the vessel or conduit.

20. The apparatus for sampling or feeding a flowable material through a wall of a vessel or conduit according to claim 1, wherein the vessel or conduit has a single opening formed through the wall thereof, and said body extends through said opening and only partially into an interior of the vessel or conduit.

* * * * *